(12) United States Patent
Burdett, Jr. et al.

(10) Patent No.: US 7,729,471 B2
(45) Date of Patent: Jun. 1, 2010

(54) PRE-FILMED PRECISION SAMPLE CELL FOR X-RAY ANALYZER

(75) Inventors: John H. Burdett, Jr., Charlton, NY (US); Daniel L. Dunham, Averill Park, NY (US); James B. Quinn, Ravena, NY (US)

(73) Assignee: X-Ray Optical Systems, Inc., Armonk, NY (US)

( * ) Notice: Subject to any disclaimer, the term of this patent is extended or adjusted under 35 U.S.C. 154(b) by 69 days.

(21) Appl. No.: 12/323,590

(22) Filed: Nov. 26, 2008

(65) Prior Publication Data

US 2009/0141867 A1 Jun. 4, 2009

Related U.S. Application Data

(60) Provisional application No. 60/991,396, filed on Nov. 30, 2007.

(51) Int. Cl.
*G01N 23/223* (2006.01)
*B01L 3/00* (2006.01)

(52) U.S. Cl. .......................... 378/47; 378/45; 378/204; 378/208; 73/864.91

(58) Field of Classification Search .................... 378/44, 378/45, 46, 47, 48, 49, 71, 72, 76, 79, 80, 378/204, 208; 73/864.91; 422/102
See application file for complete search history.

(56) References Cited

U.S. PATENT DOCUMENTS

| | | | |
|---|---|---|---|
| 2,436,291 A | | 2/1948 | Daniel |
| 3,378,684 A | * | 4/1968 | Mentink et al. .............. 250/428 |
| 3,462,598 A | * | 8/1969 | Burke et al. ................... 378/47 |
| 4,037,109 A | | 7/1977 | Hosokawa et al. |
| 4,115,689 A | * | 9/1978 | Won ............................. 378/47 |
| 4,346,299 A | | 8/1982 | Mitteldorf et al. |

(Continued)

FOREIGN PATENT DOCUMENTS

WO   WO2006/021961 A   3/2006

OTHER PUBLICATIONS

International Search Report and Written Opinion from International Application No. PCT/US2008/084800 completed Mar. 13, 2009, and mailed on Mar. 19, 2009.

*Primary Examiner*—Allen C. Ho
(74) *Attorney, Agent, or Firm*—Jeffrey R. Klembczyk, Esq.; Kevin P. Radigan, Esq.; Heslin Rothenberg Farley & Mesiti P.C.

(57) ABSTRACT

A sample cell for an analysis instrument, having an outer body forming a sample reservoir therein; a directional fill valve disposed in an upper end of the outer body and forming an upper end of the sample reservoir, the fill valve for accepting a sample during filling, and preventing sample leakage while providing venting after filling; and a film covering a lower end of the outer body, and forming a bottom end of the sample reservoir, the film for presenting the sample to an analysis focal spot of the analysis instrument. The disclosed sample cell is especially suited for an x-ray analysis engine having a focal spot requiring alignment with the sample in the sample cell. At least one x-ray optic may be disposed in an excitation and/or detection path, requiring alignment to the focal spot, in e.g., a WDXRF or EDXRF system.

20 Claims, 5 Drawing Sheets

U.S. PATENT DOCUMENTS

| | | |
|---|---|---|
| 4,409,854 A | 10/1983 | Solazzi |
| 4,448,311 A | 5/1984 | Houser |
| 4,575,869 A * | 3/1986 | Torrisi et al. .................. 378/47 |
| 4,587,666 A | 5/1986 | Torrisi et al. |
| 4,620,648 A | 11/1986 | Schwartzman |
| 4,643,033 A | 2/1987 | Sloazzi |
| 4,665,759 A | 5/1987 | Solazzi |
| 4,698,210 A | 10/1987 | Solazzi |
| 4,728,006 A | 3/1988 | Drobish et al. |
| 4,991,745 A | 2/1991 | Brown |
| 5,253,280 A | 10/1993 | Mizuta |
| 5,323,441 A | 6/1994 | Torrisi et al. |
| 5,351,281 A * | 9/1994 | Torrisi et al. .................. 378/79 |
| 5,409,144 A | 4/1995 | Brown |
| 5,439,143 A | 8/1995 | Brown et al. |
| 5,451,375 A | 9/1995 | Solazzi |
| 5,454,020 A | 9/1995 | Solazzi |
| 5,630,989 A | 5/1997 | Solazzi |
| 5,703,927 A * | 12/1997 | Torrisi et al. ................. 378/208 |
| 5,712,891 A * | 1/1998 | Benony et al. ................. 378/47 |
| 5,832,054 A * | 11/1998 | Kuwabara .................... 378/45 |
| 5,971,232 A | 10/1999 | Rohr et al. |
| 6,009,766 A | 1/2000 | Solazzi |
| 6,012,325 A * | 1/2000 | Ma ........................... 73/24.02 |
| 6,045,004 A | 4/2000 | Elliott |
| 6,089,419 A | 7/2000 | Gross |
| 6,233,307 B1 * | 5/2001 | Golenhofen ................. 378/45 |
| 6,361,744 B1 | 3/2002 | Levy |
| 6,428,751 B1 | 8/2002 | Solazzi |
| 6,603,544 B1 | 8/2003 | Eckert |
| 6,651,305 B2 | 11/2003 | Fassbind et al. |
| D490,332 S | 5/2004 | Sandor |
| D501,802 S | 2/2005 | Sandor |
| 6,955,099 B2 | 10/2005 | Goodin |

* cited by examiner

PRE-FILMED PRECISION SAMPLE CELL FOR X-RAY ANALYZER

CROSS-REFERENCE TO RELATED PATENT APPLICATION

This application claims the benefit of U.S. provisional patent application Ser. No. 60/991,396, filed Nov. 30, 2007, which is hereby incorporated by reference in its entirety.

TECHNICAL FIELD

This invention relates in general to sample handling cells for sample analysis, and in particular to a precision sample cell for an x-ray analyzer where minimization of contamination and precise positioning are required, especially for liquid samples.

BACKGROUND OF THE INVENTION

X-ray analysis of liquids is a growing area of interest across many industries such as medical, pharmaceutical, and petroleum. U.S. Pat. Nos. 6,934,359 and 7,072,439, incorporated by reference herein in their entirety and assigned to X-Ray Optical Systems, Inc., the assignee of the present invention, disclose monochromatic wavelength dispersive x-ray fluorescence (MWD XRF) techniques and systems for the analysis of liquid samples. As one particular example, these patents disclose techniques for the determination of the level of sulfur in petroleum fuels, and a commercialized analyzer (SINDIE) is now in widespread use for this measurement at petroleum refining, pipeline, and terminal facilities.

Recent government mandates of sulfur levels in diesel fuel below 15 parts per million (ppm) resulted in the need for instruments with limits of detection much lower than 15 ppm. Certain commercial versions of the SINDIE analyzer perform at limits of detection of less than one (1) ppm.

To maintain this level of performance, repeatability, and reproduceability, in potentially diverse measurement environments, sample presentation to the x-ray analyzer engine must be effectuated carefully and accurately. Not only must the sample be free from any contamination, but the sample cell itself must be free from contamination on its critical surfaces. Moreover, sample cell venting is critical (especially for petroleum applications), and adequate containment of the petroleum is also important. The sample cell must remain generally immune from a number of operator errors.

Finally, the sample cell must present the sample to the x-ray measurement engine at a precise distance (along a z-axis as discussed below) for proper alignment to the requisite x-ray analysis spot. This z-axis alignment is critically important for x-ray optic enabled analyzers (such as those disclosed in the above-incorporated U.S. Patents and discussed further below) because of the sensitivity of the measurement to the focal spots of one or two separate optics in the x-ray excitation and/or detection paths.

What is required, therefore, is a precisely formed sample cell for x-ray analysis applications, which minimizes contamination, minimizes the potential for operator-induced errors, and which provides precise alignment of a sample to an x-ray analyzer engine, especially an x-ray optic-enabled analyzer engine.

SUMMARY OF THE INVENTION

The shortcomings of the prior art are overcome and additional advantages are provided by the present invention which in one aspect is a sample cell for an analysis instrument, having an outer body forming a sample reservoir therein; a directional fill valve disposed in an upper end of the outer body and forming an upper end of the sample reservoir, the fill valve for accepting a sample during filling, and preventing sample leakage while providing venting after filling; and a film covering a lower end of the outer body, and forming a bottom end of the sample reservoir, the film for presenting the sample to an analysis focal spot of the analysis instrument. A ring may be used for film around the body, which upon fastening remains around the body over the film. In one embodiment, the ring may be placed in a cylindrical cavity formed between the inner and outer walls of the outer body of the sample cell.

The fill valve may be a one-way, elastomeric fill valve to accommodate a pipette during sample filling fixedly fastening the, preventing leakage of the sample upon removal of the pipette, while providing venting of the reservoir after filling.

The sample cell is especially suited for an x-ray analysis engine having a focal spot requiring alignment with the sample in the sample cell. At least one x-ray optic may be disposed in an excitation and/or detection path, requiring alignment to the focal spot, in e.g., an WDXRF or EDXRF system.

The majority (or all) of the assembly may take place at the factory-eliminating operator error while still preserving a level of part interchangeability. Contamination is prevented using the closeable fill valve disclosed, as well as a spatially insulated film at the lower end of the reservoir. Finally, the precise formation and alignment features of the present invention ensure precise alignment in an x-ray analysis system, thereby improving measurement accuracy and reliability.

Further additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in connection with the accompanying drawings in which:

DETAILED DESCRIPTION OF THE INVENTION

Figure 1:
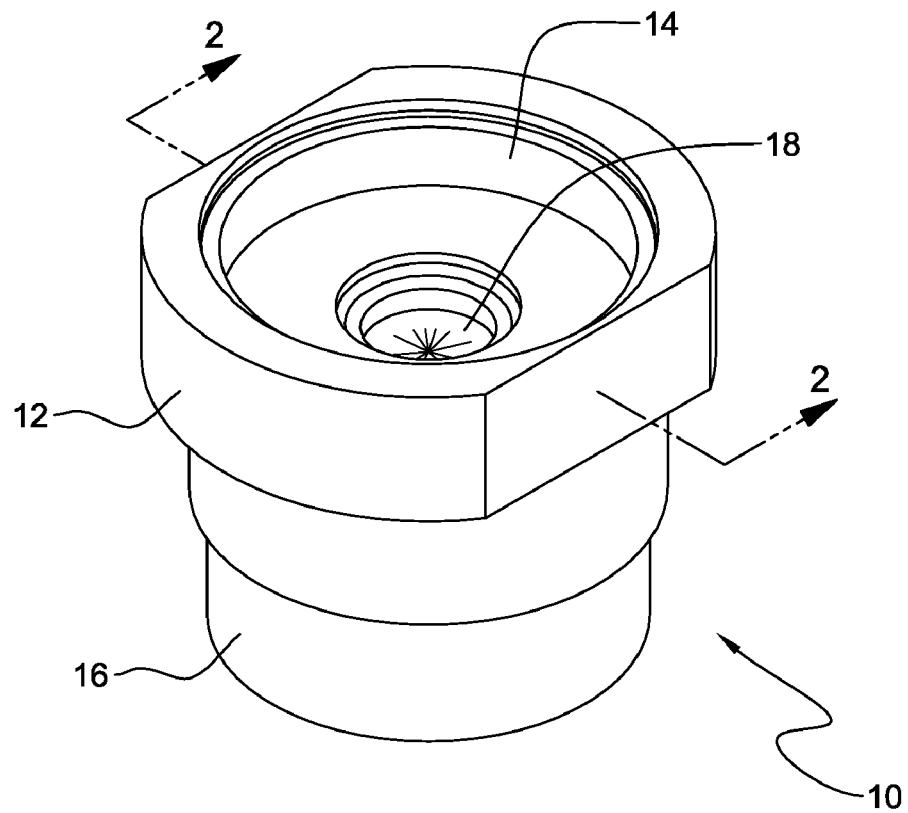
FIG. 1 is a perspective view of a sample cell, in accordance with an aspect of the present invention.
Figure 2:
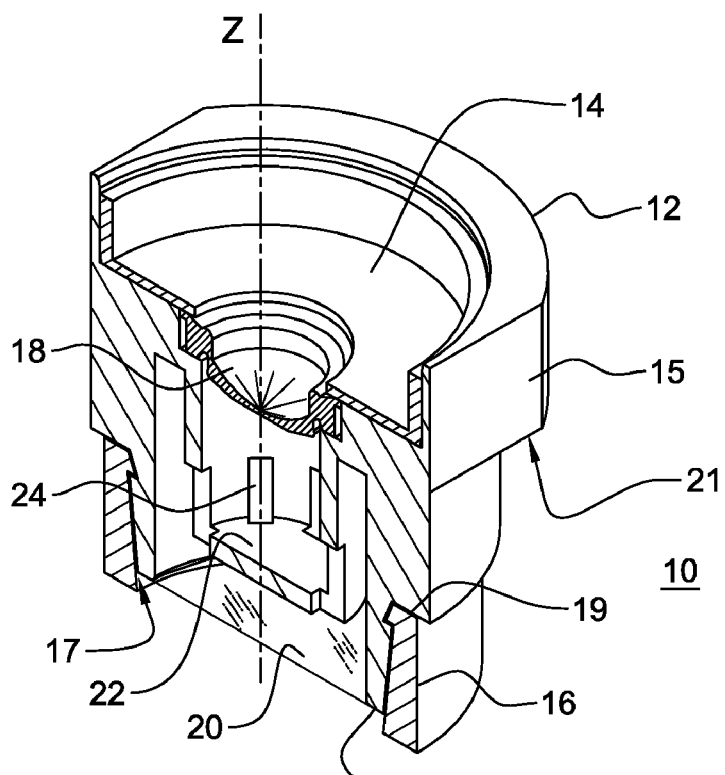
FIG. 2 is a sectional view of the sample cell of FIG. 1.
Figure 3:
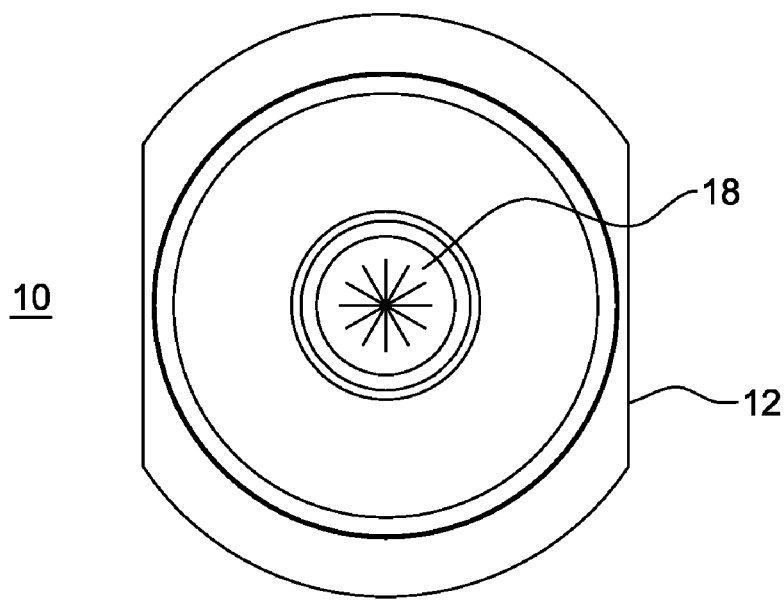
FIG. 3 is a top view of the sample cell of FIG. 1.
Figure 4:
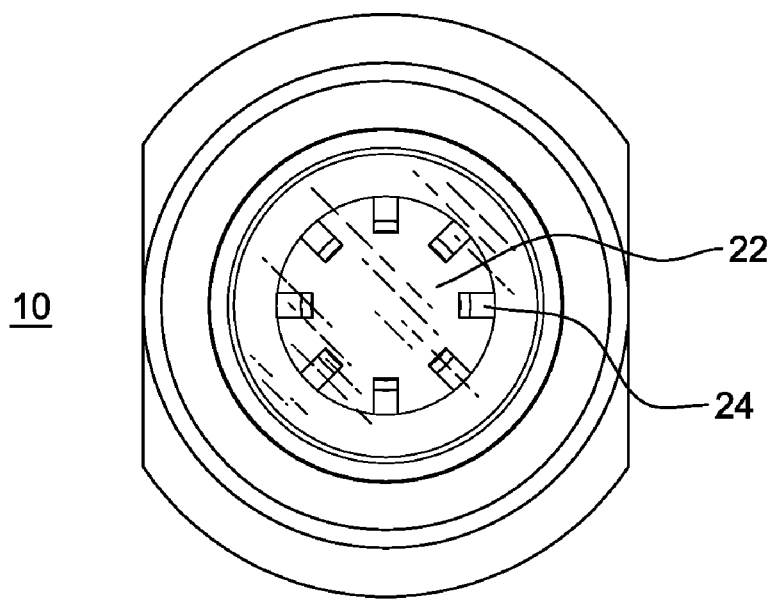
FIG. 4 is a bottom view of the sample cell of FIG. 1.

In accordance with a first aspect of the present invention, and with reference to FIGS. 1-4 (where like elements are referred to using like element numbers), a pre-filmed, precision sample cell 10 is provided. The sample cell includes an outer body 12 forming an interior sample reservoir, an upper end of which includes a fill valve 18 held in place by an exemplary friction-fitted cap 14.

The fill valve is preferably directional, i.e. 1-way to allow a sample in (via a pipette or other insertion device), but preventing a sample from leaking out. The SUREFLO or MEDIFLO directional elastomeric valves available from Liquid Molding Systems, Inc. are examples of such directional valves. Such valves can also be designed/chosen to provide an adequate venting capability of the sample reservoir in one embodiment.

The lower end of the interior sample reservoir is formed of a film 20 (e.g., mylar) which can be wrapped tightly around the lower ends 13 of the body 12, and held in place using a conformal ring. Other attachment techniques are possible, including glues, ultrasonic, RF, or other heating techniques to create a bond between the film and the body around the perimeter of the lower ends 13. The film is preferably designed with enough strength to hold the sample (and, as discussed further below, with enough strength to support the entire sample cell in the instrument), while allowing penetration of x-rays, and resultant x-ray fluorescence to/from the x-ray analysis engine. The sample can be a liquid sample, a partially-liquid sample, or a solid (e.g., powder) sample.

Film 20 may be fastened in place around the lower edge 13 of the body 12 using a conformal ring 16. In one embodiment, the ring snaps into place using barbed-shaped edges which mate with complimentary surfaces in region 19, or another snapping technique which provides an essentially permanent fit to discourage or prevent disassembly. In accordance with this aspect of the present invention, friction-fit cap 14, and/or snapping ring 16, are designed to be essentially, permanently, mounted on the body 12. This permanent mounting can be effected using friction for the cap 14, and 1-way barbs 19 for ring 16. Such permanent mounting (i.e., at a precision assembly facility) ensures that the fill valve is precisely placed, and/or the film is precisely mounted. This precise, factory-set mounting ensures precision placement, discourages tampering in the field, while allowing some level of component interchangeability, including the ability to use cut pieces of film purchased in volume, and different types of films or fill valves.

In accordance with another aspect of the present invention, an edge of the ring 16 extends beyond the lower end 13 of the body over which the film is fastened forming a recessed area 17. The sample cell can then rest upon the lower edge of ring 16, when placed on a surface, with the film being separated from the surface by a distance corresponding to the depth of the recess. This prevents contamination of the outer surface of the film 20 when the sample cell is in use.

A blocking structure 22 can also be provided within the reservoir to prevent an inserted pipette from puncturing the film 20, while allowing the sample to circulate within the reservoir. Apertures 24 in the blocking structure 22 can also be used to selectively pass certain sized particulates to the analysis area near the film.

Other features include a horizontal edge 21 which can assist/control the vertical placement of the cell in an x-ray analysis engine; and opposing faces 15 which can also be used to assist/control the horizontal/rotational placement of the cell. The precise size and film fastening of the present invention allow for precise placement of the sample along the Z axis which, as discussed above, is critical for x-ray analysis systems.

The body and other parts discussed above can be formed using injection molding of a high density, polyethylene (HDPE) compound, PET, or polypropylene.

In accordance with another embodiment of the present invention, and with reference to FIGS. 5-8 (where like elements are referred to using like element numbers), a pre-filmed, precision sample cell 110 is provided. The sample cell includes an outer body 112 forming an interior sample reservoir, an upper end of which includes a fill valve 118 held in place by an exemplary snap-in cap 114.

The fill valve is preferably directional, i.e., 1-way to allow a sample in (via a pipette or other insertion device), but preventing a sample from leaking out. The SUREFLO or MEDIFLO directional elastomeric valves available from Liquid Molding Systems, Inc. are examples of such directional valves. Such valves can also be designed/chosen to provide an adequate venting capability of the sample reservoir in one embodiment.

The lower end of the interior sample reservoir is formed of a film 120 (e.g., mylar) which can be wrapped tightly around a certain lower edge 113 of the body 112, and held in place using a conformal ring 116. Other attachment techniques are possible, including glues, ultrasonic, RF, or other heating techniques to create a bond between the film and the body around the perimeter of the lower edges 113. The film is preferably designed with enough strength to hold the sample (and, as discussed further below, with enough strength to support the entire sample cell in the instrument), while allowing penetration of x-rays, and resultant x-ray fluorescence to/from the x-ray analysis engine. The sample can be a liquid sample, a partially-liquid sample, or a solid (e.g., powder) sample.

Film 120 may be fastened in place around the lower edge 113 of the body 112 using a conformal ring 116. In one embodiment, the ring 116 is frictionally held in place between an outer wall 128 and an inner wall 126 formed, e.g. as integral parts of the body 112. This method provides an essentially permanent fit to discourage or prevent disassembly, with ring 116 pushed into the cylindrical cavity formed between walls 126 and 128. In accordance with this aspect of the present invention, snap-in cap 114, and/or friction ring 116, are designed to be essentially, permanently, mounted on the body 112. Permanent mounting for cap 114 can be effected using 1-way barbs where one side of the snap-in cap 114 has a barbed-shape edge which mates with the complimentary structure of the body. Permanent mounting for the ring 116 can be effected using friction between the ring and the inner and/or outer walls. Such permanent mounting (i.e., at a precision assembly facility) ensures that the fill valve is precisely placed, and/or the film is precisely mounted. This precise, factory-set mounting ensures precision placement, discourages tampering in the field, while allowing some level of component interchangeability, including the ability to use cut pieces of film purchased in volume, and different types of films or fill valves.

In accordance with another aspect of the present invention, the lower edge of outer wall 128 extends beyond the lower edge of 113 of inner wall 126 over which the film is fastened, thereby forming a recessed area 117. The sample cell can then rest upon the outer wall 128 when placed on a surface, with the film being separated from the surface by a distance corresponding to the depth of the recess. This prevents contamination of the outer surface of the film 120 when the sample cell is in use.

A blocking structure 122 can also be provided within the reservoir to prevent an inserted pipette from puncturing the film 120, while allowing the sample to circulate within the reservoir. Apertures 124 in the blocking structure 122 can also be used to selectively pass certain sized particulates to the analysis area near the film. One aperture, e.g., a hole 125, is provided at the bottom of blocking structure 122 and is large enough to allow the sample to pass through to the film without upward splatter, but small enough to prevent the pipette from passing through and puncturing the film.

Other features include a horizontal edge 121 which can assist/control the vertical placement of the cell in an x-ray analysis engine; and opposing faces 115 which can also be used to assist/control the horizontal/rotational placement of the cell. The precise size and film fastening of the present invention allow for precise placement of the sample along the Z axis which, as discussed above, is critical for x-ray analysis systems.

Figure 5:
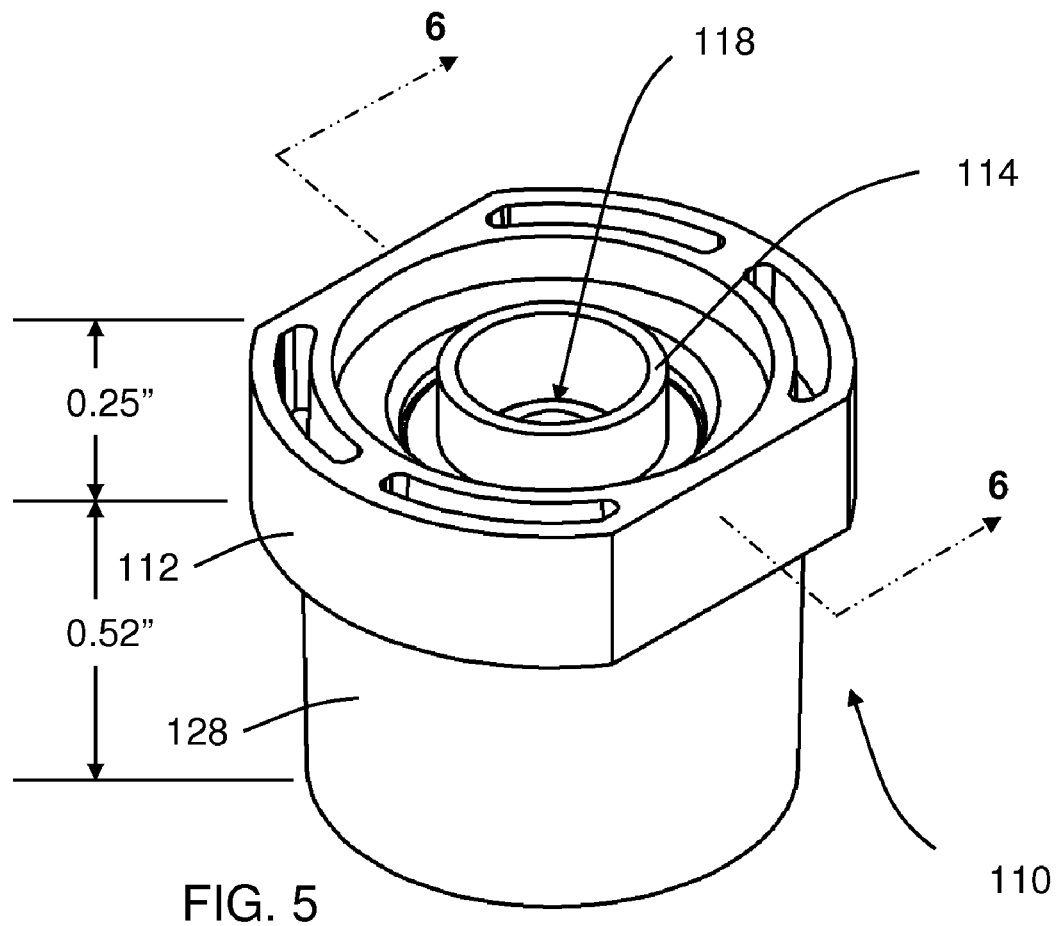
FIG. 5 is perspective view of a sample cell, in accordance with another aspect of the invention.
Figure 6:
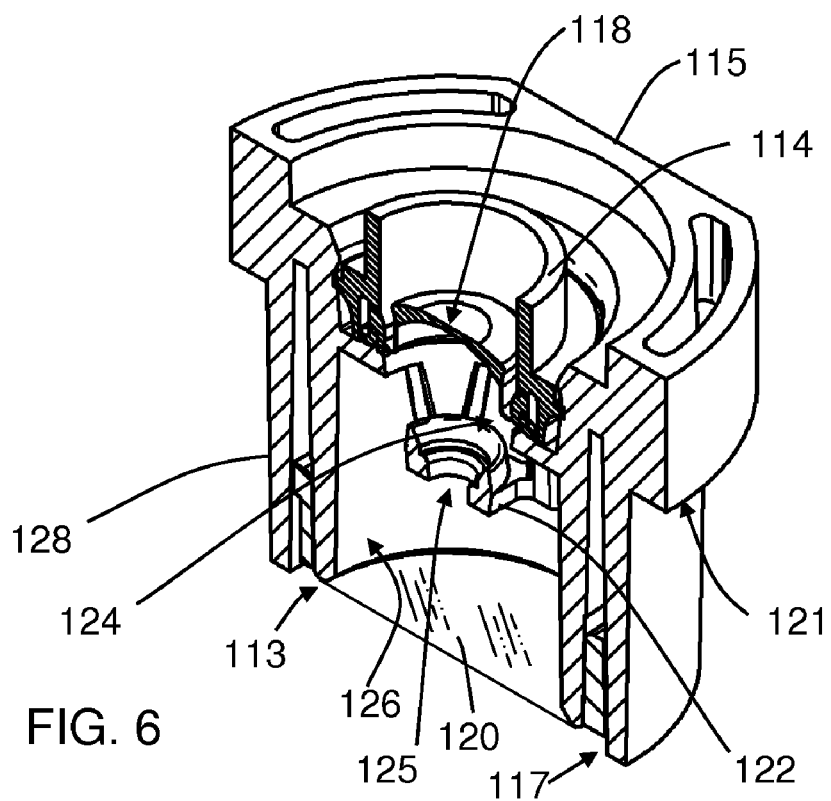
FIG. 6 is a sectional view of the sample cell of FIG. 5.
Figure 7:
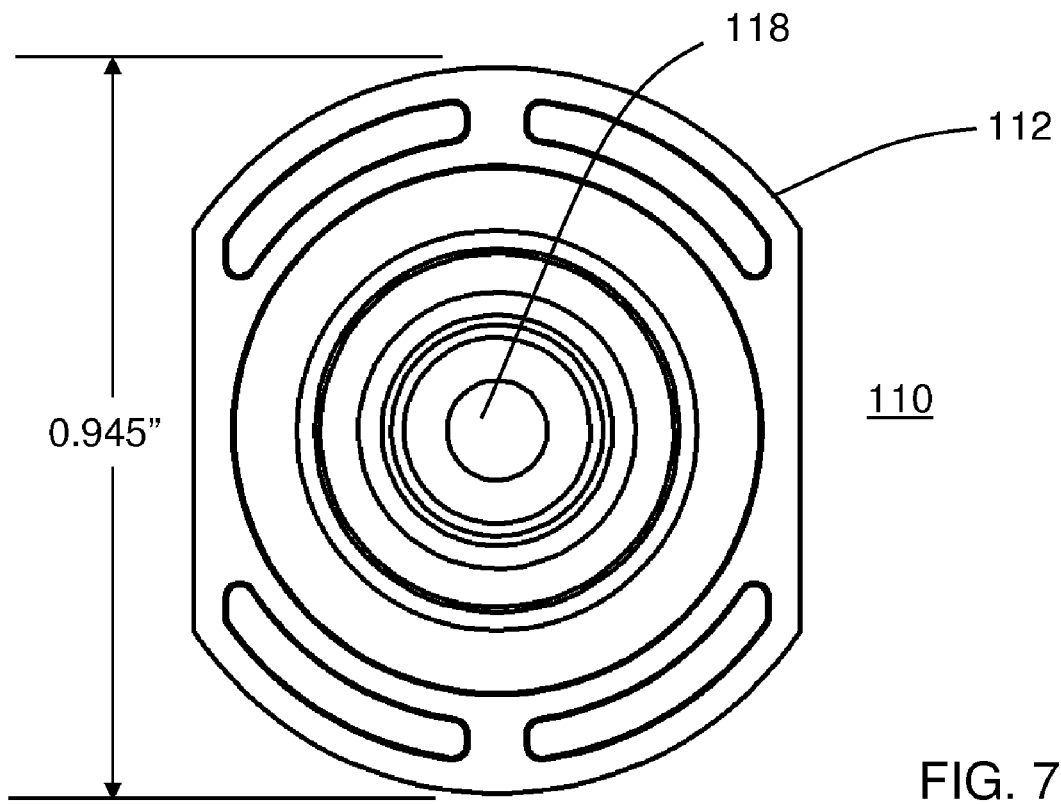
FIG. 7 is a top view of the sample cell of FIG. 5.
Figure 8:
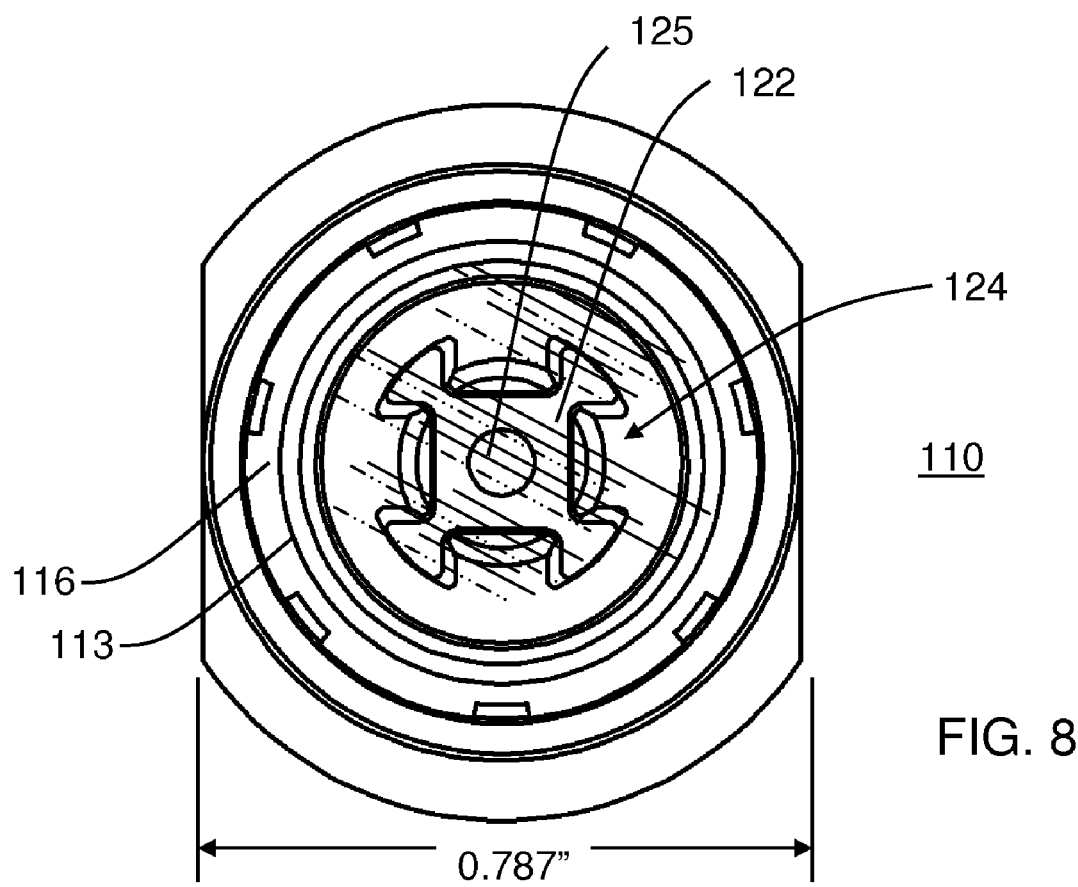
FIG. 8 is a bottom view of the sample cell of FIG. 5.

Certain exemplary dimensions are shown in FIGS. 5, 7, and 8; which convey the rather small size of the sample cell of the present invention in comparison to the known approaches. The overall height of the sample cell is less than about 0.8 inches, and the outer diameter is less than about 1.0 inch. In general, variations of about +/−25% from the depicted dimensions are considered to fall within the principles of the present invention.

Those skilled in the art will recognize that any combination of the features of the first (FIGS. 1-4) and second (FIGS. 5-8) embodiments of the present invention can be combined without departing from the principles of the present invention.

Figure 9:
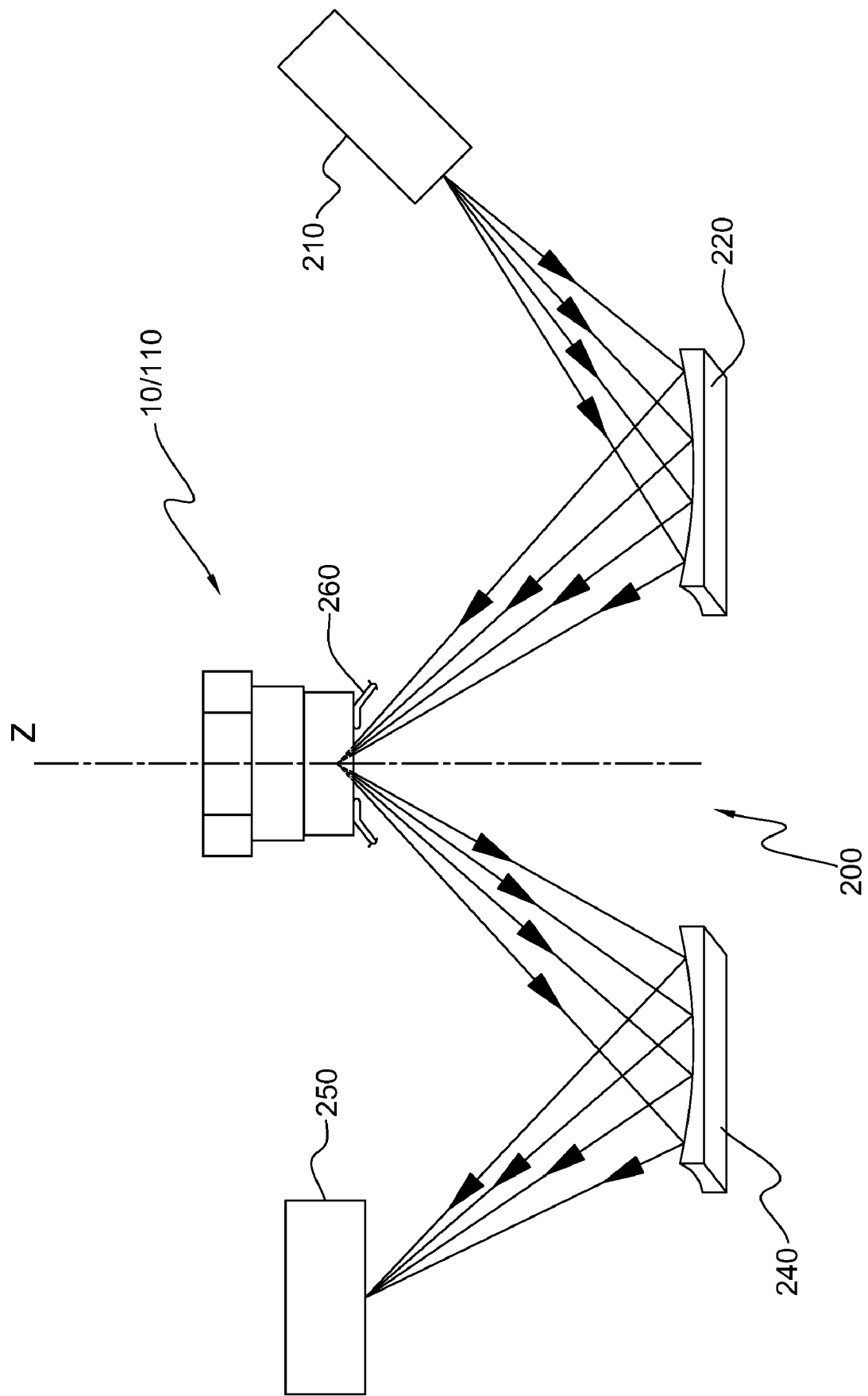
FIG. 9 is a schematic view of the sample cell of the present invention aligned to a focal spot of an x-ray optic-enabled x-ray analysis engine, according to another aspect of the present invention.

FIG. 9 depicts in schematic view an exemplary MWD XRF x-ray analysis engine 200 in combination with a sample cell 10 or 110. The x-ray analysis engine has a focal spot requiring alignment with the sample in the sample cell. Engine 200 includes, in one embodiment, an x-ray source 210 and detector 250. X-ray optics 220 and/or 240 can be placed in the excitation and/or detection paths of the engine. These optics require a high degree of alignment with the sample spot to function at the requisite limits of detection discussed above. Such optics include, for example, curved crystal monochromating optics such as those disclosed in commonly assigned U.S. Pat. Nos. 6,285,506; 6,317,483; and 7,035,374; and/or multilayer optics such as those disclosed in commonly assigned U.S. Patent Application entitled "X-Ray Focusing Optic Having Multiple Layers With Respective Crystal Orientations," U.S. Ser. No. 11/941,377 filed Nov. 16, 2007; and/or polycapillary optics such as those disclosed in commonly assigned U.S. Pat. Nos. 5,192,869; 5,175,755; 5,497,008; 5,745,547; 5,570,408; and 5,604,353. Optic/source combinations such as those disclosed in commonly assigned U.S. Pat. Nos. 7,110,506 and 7,209,545 are also useable. Each of the above-noted patents and patent applications is incorporated herein by reference in its entirety.

Curved monochromating optics in the excitation and detection path are shown in FIG. 9, which is the configuration of the SINDIE sulfur analyzer discussed above. However, an optic may only be present in one of these paths, which still requires precise alignment. In one example, an optic of any of the above-describe types may only be present in the excitation path, and the detection path would include an energy dispersive detector. This is the common configuration of an energy dispersive x-ray fluorescence (EDXRF) system.

In one embodiment, to ensure precision alignment of the sample to the focal spot, the sample cell could rest on one or more supports 260 which directly contact the film. The upper surfaces (not visible) of the supports are positioned in the instrument to correspond to the focal spot, and when the film surface rests on the supports, precise alignment is ensured.

The sample cell of the present invention provides important advantages. The majority (or all) of the assembly takes place at the factory-eliminating operator error while still preserving a level of part interchangeability. Contamination is prevented using the closeable fill valve disclosed, as well as a spatially insulated film at the lower end of the reservoir. Finally, the precise formation and alignment features of the present invention ensure precise alignment in an x-ray analysis system, thereby improving measurement accuracy and reliability.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. A sample cell for an analysis instrument, comprising:
an outer body forming a sample reservoir therein;
a directional fill valve disposed in an upper end of the outer body and forming an upper end of the sample reservoir, the fill valve for accepting a sample during filling, and preventing sample leakage while providing venting after filling; and
a film covering a lower edge of the outer body, and forming a bottom end of the sample reservoir, the film for presenting the sample to an analysis focal spot of the analysis instrument.

2. The sample cell of claim 1, further comprising a ring for fixedly fastening the film around the lower edge of the body, which upon fastening remains around the lower edge of the body over the film.

3. The sample cell of claim 2, wherein an edge of the ring extends beyond the lower end of the body over which the film is fastened, upon which the sample cell can rest when placed on a surface, the film being thereby separated from the surface by a distance corresponding to the size of the extension.

4. The sample cell of claim 2, wherein the outer body includes an inner wall and an outer wall between which the ring is frictionally held, and a lower edge of the inner wall comprises the edge around which the film is fastened.

5. The sample cell of claim 4, wherein the outer wall extends beyond the lower edge of the inner wall over which the film is fastened, upon which the sample cell can rest when placed on a surface, the film being thereby separated from the surface by a distance corresponding to the size of the extension.

6. The sample cell of claim 1, wherein the fill valve is a one-way, elastomeric fill valve to accommodate a pipette during sample filling, preventing leakage of said sample upon removal of the pipette, while providing venting of the reservoir upon filling.

7. The sample cell of claim 6, further comprising a blocking structure formed within the sample reservoir and aligned to the fill valve, to prevent the pipette from reaching the film through the sample reservoir upon insertion into the fill valve.

8. The sample cell of claim 7, where the blocking structure allows at least some of the sample to circulate beyond the blocking structure.

9. The sample cell of claim 8, wherein the blocking structure includes apertures to allow particulate matter of the sample of a predetermined size to circulate beyond the blocking structure, while preventing particulate matter exceeding said size from circulating beyond the blocking structure.

10. The sample cell of claim 9, wherein one of the apertures of the blocking structure comprises a hole in the bottom of the blocking structure large enough to promote a downward flow of the sample without splatter, but small enough prevent the pipette from reaching the film through the blocking structure upon insertion into the fill valve.

11. The sample cell of claim 1, wherein the film is essentially permanently attached around the body using an essentially permanently mounted ring.

12. The sample cell of claim 11, further comprising a cap, essentially permanently fitted into an upper portion of the body, to hold the fill valve in place.

13. The sample cell of claim 1, further comprising a cap, essentially permanently fitted into an upper portion of the body, to hold the fill valve in place.

14. A combination comprising: an x-ray analysis engine; and the sample cell of claim 1, wherein the x-ray analysis engine having a focal spot requiring alignment with the sample in the sample cell.

15. The combination of claim 14, further comprising at least one x-ray optic disposed in an excitation and/or detection path, requiring alignment to the focal spot.

16. The combination of claim 15, wherein the at least one x-ray optic comprises a curved monochromating optic or a polycapillary optic.

17. The combination of claim 15, wherein the x-ray analysis engine comprises a WDXRF analysis engine having a monochromating optic in the detection path.

18. The combination of claim 17, wherein the analysis instrument is a sulfur analysis instrument.

19. The combination of claim 15, wherein the x-ray analysis engine comprises an EDXRF analysis engine having the at least one optic in the excitation path and an energy dispersive detector in the detection path.

20. The combination of claim 15, wherein the sample cell is supported by the film in said combination using supports contacting the film of the sample cell, thereby ensuring alignment of the sample to the focal spot.

* * * * *

UNITED STATES PATENT AND TRADEMARK OFFICE
CERTIFICATE OF CORRECTION

| | | |
|---|---|---|
| PATENT NO. | : 7,729,471 B2 | Page 1 of 1 |
| APPLICATION NO. | : 12/323590 | |
| DATED | : June 1, 2010 | |
| INVENTOR(S) | : Burdett, Jr. et al. | |

It is certified that error appears in the above-identified patent and that said Letters Patent is hereby corrected as shown below:

Title Page
In the Assignee (73) delete "Armonk, NY" and insert --East Greenbush, NY--

Signed and Sealed this
Tenth Day of April, 2012

David J. Kappos
*Director of the United States Patent and Trademark Office*